US009560852B2

(12) United States Patent
Andersch et al.

(10) Patent No.: US 9,560,852 B2
(45) Date of Patent: *Feb. 7, 2017

(54) COMBINATIONS OF BIOLOGICAL CONTROL AGENTS AND INSECTICIDES OR FUNGICIDES

(75) Inventors: Wolfram Andersch, Gladbach (DE); Paul Hawen Evans, Odenthal (DE); Bernd Springer, Köln (DE); Kevin Bugg, Raleigh, NC (US); Jennifer Riggs, Raleigh, NC (US); Chi-Yu Roy Chen, Raleigh, NC (US)

(73) Assignee: Bayer Intellectual Property GmbH, Monheim (DE)

(*) Notice: Subject to any disclaimer, the term of this patent is extended or adjusted under 35 U.S.C. 154(b) by 521 days.

This patent is subject to a terminal disclaimer.

(21) Appl. No.: 12/936,700

(22) PCT Filed: Apr. 7, 2009

(86) PCT No.: PCT/EP2009/002538
§ 371 (c)(1),
(2), (4) Date: Jan. 3, 2011

(87) PCT Pub. No.: WO2009/124707
PCT Pub. Date: Oct. 15, 2009

(65) Prior Publication Data
US 2011/0110906 A1 May 12, 2011

Related U.S. Application Data

(60) Provisional application No. 61/123,254, filed on Apr. 7, 2008.

(30) Foreign Application Priority Data

Aug. 18, 2008 (EP) .................................. 08162554

(51) Int. Cl.
*A01N 63/00* (2006.01)
*A01N 63/02* (2006.01)
*A01N 43/40* (2006.01)

(52) U.S. Cl.
CPC .............. *A01N 63/02* (2013.01); *A01N 43/40* (2013.01); *A01N 63/00* (2013.01)

(58) Field of Classification Search
None
See application file for complete search history.

(56) References Cited

U.S. PATENT DOCUMENTS

| | | | |
|---|---|---|---|
| 5,215,747 A | 6/1993 | Hairston et al. |
| 6,232,270 B1 | 5/2001 | Branly et al. |
| 6,406,690 B1 | 6/2002 | Peleg et al. |
| 6,753,296 B1 | 6/2004 | Senn et al. |
| 7,718,572 B2 | 5/2010 | Igari et al. |
| 8,039,006 B2 | 10/2011 | Prato |
| 8,084,452 B2 | 12/2011 | Jeschke et al. |
| 2006/0013846 A1 | 1/2006 | Kurita et al. |
| 2009/0247551 A1 | 10/2009 | Jeschke et al. |
| 2009/0253749 A1 | 10/2009 | Jeschke et al. |
| 2010/0249193 A1 | 9/2010 | Andersch et al. |
| 2010/0305170 A1 | 12/2010 | Erdelen |

FOREIGN PATENT DOCUMENTS

| | | |
|---|---|---|
| CA | 965001 | 3/1975 |
| CA | 2146822 A1 | 10/1995 |
| DE | 22 50 085 A1 | 4/1973 |
| DE | 267 420 A1 | 5/1989 |
| EP | 0 539 588 A1 | 5/1993 |
| EP | 0 677 247 A | 10/1995 |
| FR | 2 760 600 A | 9/1998 |
| WO | WO 96/32840 A1 | 10/1996 |
| WO | WO 98/23157 A1 | 6/1998 |
| WO | WO 2007/095229 A2 | 8/2007 |
| WO | WO 2007/149134 A1 | 12/2007 |
| WO | WO 2007/149817 A2 | 12/2007 |

(Continued)

OTHER PUBLICATIONS

DeAngelis (http://www.livingwithbugs.com/use_dust.html) (2004), accessed Apr. 19, 2013.*
Cerf, et al., "Heat resistance of 'Bacillus subtilis' and 'Bacillus stearothermophilus' spores in ethylene glycol, propylene glycol and butylene glycol solutions," *Ann Microbiol (Paris)* 126(/):23-38, Masson Et Cie, Paris, France (1975).
Murrell, et al., "Initiation of Bacillus spore germination by hydrostatic pressure: effect of temperature," *Journal of Bacteriology* 129(3):1272-1280, American Society for Microbiology, United States (1977).
Powell, "Factors affecting the germination of thick suspensions of bacillus subtilis spores in L-alanine solution," *Journal of General Microbiology* 4(3):330-339, Society for General Microbiology, London, England (1950).
Vary, "Germination of Bacillus megaterium spores after various extraction procedures," *Journal of Bacteriology* 116(2):797-802, American Society for Microbiology, United States (1973).
Advisory Action mailed Jun. 17, 2013 in U.S. Appl. No. 12/867,149, Chen, et al., filed Oct. 27, 2010.
Office Action mailed Dec. 28, 2012 in U.S. Appl. No. 12/867,149, Chen, et al., filed Oct. 27, 2010.
Office Action mailed Apr. 11, 2013 in U.S. Appl. No. 12/867,149, Chen, et al., filed Oct. 27, 2010.
Office Action mailed Jan. 22, 2015 in U.S. Appl. No. 12/867,149, Chen, et al., filed Oct. 27, 2010.

(Continued)

*Primary Examiner* — Irene Marx

(57) ABSTRACT

Compositions are provided that improve overall plant vigor and yield by combining agriculturally effective amounts of at least one environmentally friendly biological control agent and at least one insect control agent and or fungicide. A composition of the present invention is particularly effective in the presence of plant parasitic nematode and fungal species. Along with a benefit of reducing insect pressure, the inventive composition enhances the root system of a plant and improves the establishment of the biological control agent within the rhizosphere, thereby enhancing the effectiveness thereof. Use of a composition of the present invention leads to an overall reduction in crop losses caused by either plant parasitic nematodes or fungi and this reduction is much greater than would have been expected from application of either component alone. Methods for utilizing compositions of the present invention are also provided. Further the compositions according to this invention display synergistic insecticidal, nematicidal, acaricidal or fungicidal activity.

8 Claims, No Drawings

(56) References Cited

FOREIGN PATENT DOCUMENTS

WO    WO 2009/126473 A1    10/2009

OTHER PUBLICATIONS

Bauer, T.A., et al., "Response of Selected Weed Species to Postemergence Imazethapyr and Bentazon," Weed Tech. 9:236-242, The Weed Science Society of America (1995).
Blackshaw, R.E., et al., "HOE-39866 Use in Chemical Fallow Systems, " Weed Tech. 3:420-428, The Weed Science Society of America (1989).
Blakcshaw, R.E., "Synergistic Mixes of DPX-A7881 and Clopyralid in Canola (Brassica napus)," Weed Tech. 3:690-695, The Weed Science Society of America (1989).
Blackshaw, R.E., et al., "Herbicide Combinations for Postemergent Weed Control in Safflower (Carthamus tinctorius)," Weed Tech. 4:97-104, The Weed Science Society of America (1990).
Blouin D.C., et al., "Analysis of Synergistic and Antagonistic Effects of Herbicides Using Nonlinear Mixed-Model Methodology," Weed Tech. 18:464-472, The Weed Science Society of America (2004).
Bradley, P.R., et al., "Response of Sorghum (Sorghum bicolor) to Atrazine, Ammonium Sulfate, and Glyphosate," Weed Tech. 14:15-18, The Weed Science Society of America (2000).
Buker, III, R.S., et al., "Confirmation and Control of a Paraquat-Tolerant Goosegrass (Eleusine indica) Biotype," Weed Tech. 16:309-313, The Weed Science Society of America (2002).
Burke, I.C., et al., "CGA-362622 Antagonizes Annual Grass Control with Clethodim," Weed Tech. 16:749-754, The Weed Science Society of America (2002).
Colby, S.R., "Calculation Synergistic and Antagonistic Responses of Herbicide Combinations," Weeds 15:20-22, Weed Society of America (1967).
Flint, J.L., et al., "Analyzing Herbicide Interactions, A Statistical Treatment of Colby's Method," Weed Tech. 2:304-309, The Weed Science Society of America (1988).
Gillespie, G.R., and Nalewaja, J.D., "Wheat (Triticum aestivum) Response to Triallate Plus Chlorsulfuron," Weed Tech. 3:20-23, The Weed Science Society of America (1989).
Green, J.M., et al., "Metribuzin and Chlorimuron Mixtures for Preemergence Broadleaf Weed Control in Soybeans, Glycine max," Weed Tech. 2:355-363, The Weed Science Society of America (1988).
Harker, K.N., and O'Sullivan, P.A., "Synergistic Mixtures of Sethoxydim and Fluazifop on Annual Grass Weeds," Weed Tech. 5:310-316 The Weed Science Society of America (1991).
Kent, L.M., et al., "Effect of Ammonium Sulfate, Imazapyr, and Enviroment on the Phytotoxicity of Imazethapyr," Weed Tech. 5:202-205, The Weed Science Society of America (1991).
Kotoula-Syka, E., et al., "Interactions between SAN 582H and Selected Safeners on Grain Sorghum (Sorghum bicolor) and Corn (Zea mays)," Weed Tech. 10:299-304, The Weed Science Society of America (1996).
Lanclos, D.Y., et al., "Glufosinate Tank-Mix Combinations in Glufosinate-Resistant Rice (Oryza sativa)," Weed Tech. 16:659-663, The Weed Science Society of America (2002).
Norris, J.L., et al., "Weed Control from Herbicide Combinations with Three Formulations of Glyphosate," Weed Tech. 15:552-558, The Weed Science Society of America (2001).
Novosel, K.M., et al., "Metolachlor Efficacy as Influenced by Three Acetolactate Synthase-Inhibiting Herbicides," Weed Tech. 12:248-253, The Weed Science Society of America (1998).
Palmer, E. W., et al., "Broadleaf Weed Control in Soybean (Glycine max) with CGA-277476 and Four Postemergence Herbicides," Weed Tech. 14:617-623, The Weed Science Society of America (2000).
Rummens, F.H.A., "An Improved Definition of Synergistic and Antagonistic Effects," Weed Science 23(1):4-6, The Weed Science Society of America, United States (1975).
Salzman, F.P., Renner, K.A., "Response of Soybean to Combinations of Clomazone, Metribuzin, Linuron, Alachlor, and Atrazine," Weed Tech. 6:922-929, The Weed Science Society of America (1992).
Scott, R.C., et al., "Spray Adjuvant, Formulation, and Enviromental Effects on Synergism from Post-Applied Tank Mixtures of SAN 582H with Fluazifop-P, Imazethapyr, and Sethoxydim," Weed Tech. 12:463-469, The Weed Science Society of America (1998).
Shaw, D.R. and Arnold, J.C., "Weed Control from Herbicide Combination with Glyphosate," Weed Tech 16:1-6, The Weed Science Society of America (2002).
Sneath, P., "Endospore-forming Gram-Positive Rods Cocci", Bergey's Manual of Systematic Bacteriology 2(13):1104-1140, Williams & Wilkins, Baltimore, MD, USA (1986).
Snipes, C.E., and Allen, R.,L., "Interaction of Graminicides Applied in Combination with Pyrithiobac," Weed Tech. 10:889-892, The Weed Science Society of America (1996).
Sun, Y.-P. & Johnson, E.R., "Analysis of Joint Action of Insecticides Against House Flies", J. Econ. Entomol, 53:887-892, United States (1960).
Tammes, P.M.L., "Isoboles, A Graphic Representation of Synergism in Pesticides," Neth. J. Plant Path. 70:73-80, Springer, Germany (1964).
Wehtje, G. and Walker, R.H., "Interaction of Glyphosate and 2,4-DB for the Control of Selected Morningglore (Ipomoea spp.) Species," Weed Tech. 11:152-156, The Weed Science Socierty of America (1997).
Zhang, W., et al., "Fenoxaprop Interaction for Barnyardgrass (Echinochloa crus-galli) Control in Rice," Weed Tech. 19:293-297, The Weed Science Society of America (2005).
Office Action mailed on Oct. 11, 2011in U.S. Appl. No. 12/814,869, inventors Erdelen, C., et al., filed Jun. 14, 2010.
International Search Report in International Application No. PCT/EP2009/002538, European Patent Office, Netherlands, mailed Dec. 12, 2010.
International Preliminary Report on Patentability with Written Opinion International Search Report in International Application No. PCT/EP2009/002538, European Patent Office, Netherlands, issued Jan. 11, 2011.
Non-Final Office Action mailed Jun. 21, 2011 in U.S. Appl. No. 12/731,812, inventors Andersch, W., et al., filed Mar. 25, 2010.
Final Office Action mailed Dec. 21, 2011 in U.S. Appl. No. 12/731,812, inventors Andersch, W., et al., filed Mar. 25, 2010.
Final Office Action mailed Dec. 19, 2012 in U.S. Appl. No. 12/731,812, inventors Andersch, W., et al., filed Mar. 25, 2010.
Final Office Action mailed May 10, 2012 in U.S. Appl. No. 12/814,869, inventors Erdelen, C., et al., filed Jun. 14, 2010.

\* cited by examiner

COMBINATIONS OF BIOLOGICAL CONTROL AGENTS AND INSECTICIDES OR FUNGICIDES

The present invention relates generally to compositions and methods for reducing overall damage and losses in plant health, vigor, and yield caused by plant parasitic nematode and fungi. More specifically, the present invention relates to compositions comprising at least one agriculturally beneficial biological control agent and at least one insect control agent as well as methods for utilizing these compositions for treating plants and plant material.

Nematodes are microscopic unsegmented worms known to reside in virtually every type of environment (terrestrial, freshwater, marine). Of the over 80,000 known species many are agriculturally significant, particularly those classified as pests. One such species is the root knot nematode which attacks a broad range of plants, shrubs and crops. These soil-born nematodes attack newly formed roots causing stunted growth, swelling or gall formation. The roots may then crack open thus exposing the roots to other microorganisms such as bacteria or fungi. With environmentally friendly practices such as reduced or no tillage farming, and various nematode species acquiring resistance to transgenic seed, nematode related crop losses appear to be on the rise.

Chemical nematicides such as soil fumigants or non-fumigants have been in use for many years to combat nematode infestations. Such nematicides may require repeated applications of synthetic chemicals to the ground prior to planting. Due to their toxicity, chemical nematicides have come under scrutiny from the Environmental Protection Agency (EPA) and in some cases their use has been limited or restricted by the EPA. As the use of traditional chemical nematicides such as methyl-bromide and organophosphates continue to be phased out, a need for the development of alternative treatment options has arisen.

One attempt to address the need is the use of biological control agents such as bacteria, fungi, beneficial nematodes, and viruses. To date, however, such efforts have proven largely ineffective from a commercial standpoint. Thus, speculation exists as to the overall effectiveness of purely biological treatments in terms of improving plant vigor and yield in agricultural regions conducive to nematode infestation.

An attempt to improve upon the efficacy of biological control agents is disclosed in WO 2007/149817. The compositions and methods disclosed in WO 2007/149817, however, rely on combinations of at least one biological control agent and at least one nematicide, such as avermectin, in an attempt to enhance plant protection against pests and pathogens. Because the mode of action of a biological nematicide can be different than that of a chemical nematicide, a combination such as this may improve the overall efficacy of the treatment, but still fails to address the somewhat greater toxicity of the chemical nematicide component. Thus, there remains a need for effective compositions and methods that not only utilize environmentally friendly biological components, but utilize them in such a manner that they can provide improved plant vigor and yield without the use of a somewhat more toxic traditional chemical nematicide such as avermectin.

Along with ever increasing crop losses caused by parasitic nematodes, there are also many such losses which can alternatively be attributed to pathogenic fungal diseases. In addition to modifications of existing chemistries and the development of new efficacious compounds or combination of chemistries, the development and use of biological fungicides are being researched.

Just as nematicidal bacteria are not always completely effective as stand alone products, fungicidal bacteria tend to work better as a compliment rather than a replacement to traditional chemistries. U.S. Pat. No. 5,215,747 describes compositions composed of *Bacillus subtilis* (a biological fungicide) and chemical fungicides to increase the overall protection from phytopathenogenic fungal species.

Compositions are provided that, in the presence of plant parasitic nematodes and/or in conditions of disease pressure facilitated by pathogenic fungal species, improve overall plant vigor and yield by combining agriculturally effective amounts of at least one biological control agent and at least one insect control agent. The biological control agent can be at least one spore-forming bacterium with proven agricultural benefit and, ideally, the ability to colonize a plant's root system. The insect control agent can be at least one chemical insecticide that, whether or not having proven direct nematicidal or fungicidal activity, does posses the proven ability to increase the mass of the plant's root system to which it is applied. The compositions of the present invention have the advantage of being either formulated into a single, stable composition with an agriculturally acceptable shelf life or being combined at the time of use (e.g., tank-mix).

The compositions according to the invention are comprised of a biological control agent, one or more components which are either insect control agents, fungicides, isoflavones or soil inoculants.

Further, the compositions according to this invention display surprisingly high degrees of insecticidal, nematicidal, acaricidal or fungicidal activity in the treatment of plants, plant parts or plant propagation material, due to a synergistic effect between the biological control agent and the insect control agents or fungicides, isoflavones or soil inoculants described in this invention.

Methods of treating a seed and/or plant are also provided. The method comprises the steps of (a) providing a composition comprising an effective amount of at least one biological control agent and at least one insect control agent and (b) applying the composition to the plant. The present compositions may be applied in any desired manner, such as in the form of a seed coating, soil drench, and/or directly in-furrow and/or as a foliar spray and applied either pre-emergence, post-emergence or both. In other words, the composition can be applied to the seed, the plant or to the fruit of the plant or to the soil wherein the plant is growing or wherein it is desired to grow.

The foregoing and other aspects of the present invention are explained in detail in the detailed description and examples set forth below.

The compositions of the present invention have been found to provide a greater degree of plant vigor and yield in nematode and fungal infested environments than would be expected from application of either the biological control agent or the insect control agent alone. At least some of the insect control agents within the scope of the present invention have been shown to provide increased root mass even in the absence of insect pressure which increased root mass leads to improved establishment of the beneficial bacteria within the rhizosphere which, in turn, reduces overall losses in crop vigor and yields caused by either plant parasitic nematodes or fungi. Along with the physical combination of these components while treating plants and plant material, in one preferred embodiment of this invention, the compositions of the present invention have been formulated to provide a stable environment for living biological control agents such as spore-forming, root-colonizing bacteria. Various additives may be added to each inventive composition depending on the desired properties for a final formulation which has the necessary physical and chemical stability to produce a commercially viable product.

The compositions of the present invention preferably include at least one biological control agent. A biological control agent as contemplated by the present invention refers to at least one spore-forming bacterium with demonstrated agricultural benefit. Preferably, the at least one spore-forming bacterium is a root-colonizing bacterium (e.g., rhizobacterium). Agricultural benefit refers to the bacterium's ability to provide a plant protection from the harmful effects of plant pathenogenic fungi and/or soil born animals such as those belonging to the phylum Nematoda or Aschelminthes. Protection against plant parasitic nematodes and fungi can occur through chitinolytic, proteolytic, collagenolytic, or other activities detrimental to these soilborne animals and/or detrimental microbial populations. Additional protection can be direct such as the production of chemicals acutely toxic to plant pests or indirect such as the induction of a systemic plant response enabling a plant to defend itself from damage caused by plant pathogens. Suitable bacteria exhibiting these nematicidal and fungicidal properties may include members of the Group B.

Group B: *Bacillus agri, Bacillus aizawai, Bacillus albolactis, Bacillus amyloliquefaciens, Bacillus firmus, Bacillus coagulans, Bacillus endoparasiticus, Bacillus endorhythmos, Bacillus firmus, Bacillus kurstaki, Bacillus lacticola, Bacillus lactimorbus, Bacillus lactis, Bacillus laterosporus, Bacillus lentimorbus, Bacillus licheniformis, Bacillus megaterium, Bacillus medusa, Bacillus metiens, Bacillus natto, Bacillus nigrificans, Bacillus popillae, Bacillus pumilus, Bacillus siamensis, Bacillus sphaericus, Bacillus spp., Bacillus subtilis, Bacillus thuringiensis, Bacillus uniflagellatus*, plus those listed in the category of *Bacillus* Genus in the "Bergey's Manual of Systematic Bacteriology, First Ed. (1986)" alone or in combination.

Alternatively Group B further comprises *Bacillus cereus*.

In a particularly preferred embodiment, the nematicidal biological control agent is at least one *B. firmus* CNCM I-1582 spore and/or *B. cereus* strain CNCM I-1562 spore as disclosed in U.S. Pat. No. 6,406,690, which is incorporated herein by reference in its entirety. In other preferred embodiments, the agriculturally beneficial bacteria is at least one *B. amyloliquefaciens* IN937a, at least one *Bacillus subtilis* strain designation GB03, or at least one *B. pumilus* strain designation GB34. Combinations of the four species of above-listed bacteria, as well as other spore-forming, root-colonizing bacteria known to exhibit agriculturally beneficial properties are within the scope and spirit of the present invention.

Particularly preferred embodiments according to the invention are also those compositions that comprise mutants of *B. firmus* CNCM I-1582 spore and/or *B. cereus* strain CNCM I-1562 spore. Very particularly those mutants, that have a nematicidal, insecticidal or plant growth promoting activity. Most particularly preferred are those mutants that have a nematicidal activity.

The amount of the at least one biological control agent employed in the compositions can vary depending on the final formulation as well as size or type of the plant or seed utilized. Preferably, the at least one biological control agent in the compositions is present in about 2% w/w to about 80% w/w of the entire formulation. More preferably, the at least one biological control agent employed in the compositions is about 5% w/w to about 65% w/w and most preferably about 10% w/w to about 60% w/w by weight of the entire formulation.

The compositions according to the present invention further comprise at least one insect control agent. In a preferred embodiment, the insect control agent can be any insecticidal chemical compound or composition having insecticidal activity, but no direct nematicidal or fungicidal activity and no detrimental activity against the utilized biological control agent, and preferably also has the added ability to increase root mass upon application. In an alternative embodiment, the compositions may comprise at least one additional chemical compound that does exhibit nematicidal or fungicidal properties. Such compositions can be useful in geographical areas having extremely high populations of nematode infestation or to provide additional fungicidal activity against heavy fungal disease pressure. The plant or plant material can be treated separately or simultaneously with the additional nematicidal or fungicidal control agent.

Suitable insect control agents according to the invention are compounds of the following groups (I1) to (I22):

The active ingredients specified in this description by their "common name" are known, for example, from "The Pesticide Manual", 13th Ed., British Crop Protection Council 2003, and from the Web page http://www.alanwood.net/pesticides.

(I1) Acetylcholinesterase (AChE) inhibitors, for example carbamates, e.g. alanycarb, aldicarb, aldoxycarb, allyxycarb, aminocarb, bendiocarb, benfuracarb, bufencarb, butacarb, butocarboxim, butoxycarboxim, carbaryl, carbofuran, carbosulfan, cloethocarb, dimetilan, ethiofencarb, fenobucarb, fenothiocarb, formetanate, furathiocarb, isoprocarb, metam-sodium, methiocarb, methomyl, metolcarb, oxamyl, pirimicarb, promecarb, propoxur, thiodicarb, thiofanox, trimethacarb, XMC, and xylylcarb; or organophosphates, e.g. acephate, azamethiphos, azinphos (-methyl, -ethyl), bromophos-ethyl, bromfenvinfos (-methyl), butathiofos, cadusafos, carbophenothion, chlorethoxyfos, chlorfenvinphos, chlormephos, chlorpyrifos (-methyl/-ethyl), coumaphos, cyanofenphos, cyanophos, chlorfenvinphos, demeton-S-methyl, demeton-S-methyl-sulphon, dialifos, diazinon, dichlofenthion, dichlorvos/DDVP, dicrotophos, dimethoate, dimethylvinphos, dioxabenzofos, disulfoton, EPN, ethion, ethoprophos, etrimfos, famphur, fenamiphos, fenitrothion, fensulfothion, fenthion, flupyrazofos, fonofos, formothion, fosmethilan, fosthiazate, heptenophos, iodofenphos, iprobenfos, isazofos, isofenphos, isopropyl, O-salicylate, isoxathion, malathion, mecarbam, methacrifos, methamidophos, methidathion, mevinphos, monocrotophos, naled, omethoate, oxydemeton-methyl, parathion (-methyl/-ethyl), phenthoate, phorate, phosalone, phosmet, phosphamidon, phosphocarb, phoxim, pirimiphos (-methyl/-ethyl), profenofos, propaphos, propetamphos, prothiofos, prothoate, pyraclofos, pyridaphenthion, pyridathion, quinalphos, sebufos, sulfotep, sulprofos, tebupirimfos, temephos, terbufos, tetrachlorvinphos, thiometon, triazophos, triclorfon, vamidothion, and imicyafos.

(I2) GABA-gated chloride channel antagonists, for example organochlorines, e.g. camphechlor, chlordane, endosulfan, gamma-HCH, HCH, heptachlor, lindane, and methoxychlor; or fiproles (phenylpyrazoles), e.g. acetoprole, ethiprole, fipronil, pyrafluprole, pyriprole, and vaniliprole.

(I3) Sodium channel modulators/voltage-dependent sodium channel blockers, for example pyrethroids, e.g. acrinathrin, allethrin (d-cis-trans, d-trans), beta-cyfluthrin, bifenthrin, bioallethrin, bioallethrin S-cyclopentyl isomer, bioethanomethrin, biopermethrin, bioresmethrin, chlovaporthrin, cis-cypermethrin, cis-resmethrin, cis-permethrin, clocythrin, cycloprothrin, cyfluthrin, cyhalothrin, cypermethrin (alpha-, beta-, theta-, zeta-), cyphenothrin, deltamethrin, empenthrin (1R isomer), esfenvalerate, etofenprox, fenfluthrin, fenpropathrin, fenpyrithrin, fenvalerate, flubrocythrinate, flucythrinate, flufenprox, flumethrin, fluvalinate, fubfenprox, gamma-cyhalothrin, imiprothrin, kadethrin, lambda-cyhalothrin, metofluthrin, permethrin (cis-, trans-), phenothrin (1R trans isomer), prallethrin, profluthrin, protrifenbute, pyresmethrin, resmethrin, RU 15525, silafluofen, tau-fluvalinate, tefluthrin, terallethrin, tetramethrin (−1R-isomer), tralomethrin, transfluthrin, ZXI 8901, pyrethrin (pyrethrum), eflusilanat;

DDT; or methoxychlor.

(I4) Nicotinergic acetylcholine receptor agonists/antagonists, for example chloronicotinyls, e.g. acetamiprid, clothianidin, dinotefuran, imidacloprid, imidaclothiz, nitenpyram, nithiazine, thiacloprid, thiamethoxam, AKD-1022, nicotine, bensultap, cartap, thiosultap-sodium, and thiocylam.

(I5) Allosteric acetylcholine receptor modulators (agonists), for example spinosyns, e.g. spinosad and spinetoram.

(I6) Chloride channel activators, for example mectins/macrolides, e.g. abamectin, emamectin, emamectin benzoate, ivermectin, lepimectin, and milbemectin; or (I7) Juvenile hormone analogues, e.g. hydroprene, kinoprene, methoprene, epofenonane, triprene, fenoxycarb, pyriproxifen, and diofenolan.

(I8) Active ingredients with unknown or non-specific mechanisms of action, for example gassing agents, e.g. methyl bromide, chloropicrin and sulfuryl fluoride;

selective antifeedants, e.g. cryolite, pymetrozine, pyrifluquinazon and flonicamid; or mite growth inhibitors, e.g. clofentezine, hexythiazox, etoxazole.

(I9) Oxidative phosphorylation inhibitors, ATP disruptors, for example diafenthiuron;

organotin compounds, e.g. azocyclotin, cyhexatin and fenbutatin oxide; or propargite, tetradifon.

(I10) Oxidative phosphorylation decouplers acting by interrupting the H proton gradient, for example chlorfenapyr, binapacryl, dinobuton, dinocap and DNOC.

(I11) Microbial disruptors of the insect gut membrane, for example *Bacillus thuringiensis* strains.

(I12) Chitin biosynthesis inhibitors, for example benzoylureas, e.g. bistrifluoron, chlorfluazuron, diflubenzuron, fluazuron, flucycloxuron, flufenoxuron, hexaflumuron, lufenuron, novaluron, noviflumuron, penfluoron, teflubenzuron or triflumuron.

(I13) Buprofezin.

(I14) Moulting disruptors, for example cyromazine.

(I15) Ecdysone agonists/disruptors, for example diacylhydrazines, e.g. chromafenozide, halofenozide, methoxyfenozide, tebufenozide, and Fufenozide (JS118); or azadirachtin.

(I16) Octopaminergic agonists, for example amitraz.

(I17) Site III electron transport inhibitors/site II electron transport inhibitors, for example hydramethylnon; acequinocyl; fluacrypyrim; or cyflumetofen and cyenopyrafen.

(I18) Electron transport inhibitors, for example

Site I electron transport inhibitors, from the group of the METI acaricides, e.g. fenazaquin, fenpyroximate, pyrimidifen, pyridaben, tebufenpyrad, tolfenpyrad, and rotenone; or voltage-dependent sodium channel blockers, e.g. indoxacarb and metaflumizone.

(I19) Fatty acid biosynthesis inhibitors, for example tetronic acid derivatives, e.g. spirodiclofen and spiromesifen; or tetramic acid derivatives, e.g. spirotetramat.

(I20) Neuronal inhibitors with unknown mechanism of action, e.g. bifenazate.

(I21) Ryanodine receptor effectors, for example diamides, e.g. flubendiamide, (R),(S)-3-chloro-N$^1$-{2-methyl-4-[1,2,2,2-tetrafluoro-1-(trifluoromethyl)ethyl]phenyl}-N$^2$-(1-methyl-2-methylsulphonylethyl)phthalamide, chlorantraniliprole (Rynaxypyr), or Cyantraniliprole (Cyazypyr).

(I22) Further active ingredients with unknown mechanism of action, for example amidoflumet, benclothiaz, benzoximate, bromopropylate, buprofezin, chinomethionat, chlordimeform, chlorobenzilate, clothiazoben, cycloprene, dicofol, dicyclanil, fenoxacrim, fentrifanil, flubenzimine, flufenerim, flutenzin, gossyplure, japonilure, metoxadiazone, petroleum, potassium oleate, pyridalyl, sulfluramid, tetrasul, triarathene or verbutine; or one of the following known active compounds:

4-{[(6-brompyrid-3-yl)methyl](2-fluorethyl)amino}furan-2(5H)-on (known from WO 2007/115644), 4-{[(6-fluorpyrid-3-yl)methyl](2,2-difluorethyl)amino}furan-2(5H)-on (known from WO 2007/115644), 4-{[(2-chlor-1,3-thiazol-5-yl)methyl](2-fluorethyl)amino}furan-2(5H)-on (known from WO 2007/115644), 4-{[(6-chlorpyrid-3-yl)methyl](2-fluorethyl)amino}furan-2(5H)-on (known from WO 2007/115644), 4-{[(6-chlorpyrid-3-yl)methyl](2,2-difluorethyl)amino}furan-2(5H)-on known from WO 2007/115644), 4-{[(6-chlor-5-fluorpyrid-3-yl)methyl](methyl)amino}furan-2(5H)-on (known from WO 2007/115643), 4-{[(5,6-dichlorpyrid-3-yl)methyl](2-fluorethyl)amino}furan-2(5H)-on (known from WO 2007/115646), 4-{[(6-chlor-5-fluorpyrid-3-yl)methyl](cyclopropyl)amino}furan-2(5H)-on (known from WO 2007/115643), 4-{[(6-chlorpyrid-3-yl)methyl](cyclopropyl)amino}furan-2(5H)-on (known from EP-A-0 539 588), 4-{[(6-chlorpyrid-3-yl)methyl](methyl)amino}furan-2(5H)-on (known from EP-A-0 539 588), [(6-chlorpyridin-3-yl)methyl](methyl)oxido-λ$^4$-sulfanylidencyanamid (known from WO 2007/149134), [1-(6-chlorpyridin-3-yl)ethyl](methyl)oxido-λ$^4$-sulfanylidencyanamid (known from WO 2007/149134) and its diastereomeres (A) and (B)

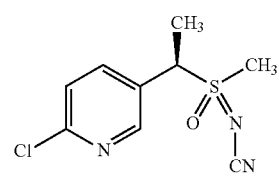

(A)

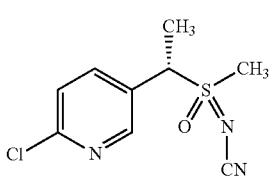

(also known from WO 2007/149134), [(6-trifluormethyl-pyridin-3-yl)methyl](methyl)oxido-$\lambda^4$-sulfanylidencyanamid (known from WO 2007/095229), or [1-(6-trifluormethylpyridin-3-yl)ethyl](methyl)oxido-$\lambda^4$-sulfanylidencyanamid (known from WO 2007/149134) and its diastereomeres (C) and (D), namely Sulfoxaflor

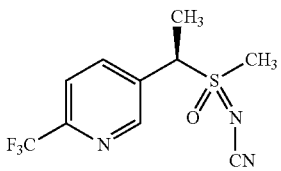

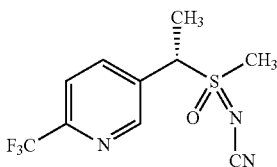

(also known from WO 2007/149134).

The compositions according to the invention comprise one biological control agent and at least one insect control agent selected from groups (I1) to (I22).

In a preferred embodiment the compositions according to the invention comprise a biological control agent, which is *Bacillus firmus* strain CNCM I-1582 spore and at least one fungicide selected from the list insect control agent selected from groups (I1) to (I22).

In another preferred embodiment the compositions according to the invention comprise a biological control agent, which is *Bacillus cereus* strain CNCM I-1562 spore and at least one fungicide selected from the insect control agent selected from groups (I1) to (I22).

In a preferred embodiment, the insect control agent is selected from the group:
Clothianidin, imidacloprid, thiacloprid, thiamethoxam, acetamiprid, methiocarb, thiodicarb, beta-cyfluthrin, cyfluthrin, deltamethrin, tefluthrin, indoxacarb, spinosad, spinetoram, fipronil, ethiprole, emamectin-benzoate, avermectin, spirodiclofen, spiromesifen, spirotetramat, flubendiamide, (R),(S)-3-chloro-N$^1$-{2-methyl-4-[1,2,2,2-tetrafluoro-1-(trifluoromethyl)ethyl]phenyl}-N$^2$-(1-methyl-2-methylsulphonylethyl)phthalamide, chlorantraniliprole (Rynaxypyr), or Cyantraniliprole (Cyazypyr), sulfoxaflor, In another preferred embodiment, the insect control agent is transfluthrin.

In another preferred embodiment, the insect control agent is selected from the group: 4-{[(6-brompyrid-3-yl)methyl](2-fluorethyl)amino}furan-2(5H)-on (known from WO 2007/115644), 4-{[(6-fluorpyrid-3-yl)methyl](2,2-difluorethyl)amino}furan-2(5H)-on (known from WO 2007/115644), 4-{[(2-chlor-1,3-thiazol-5-yl)methyl](2-fluorethyl)amino}furan-2(5H)-on (known from WO 2007/115644), 4-{[(6-chlorpyrid-3-yl)methyl](2-fluorethyl)amino}furan-2(5H)-on (known from WO 2007/115644), 4-{[(6-chlorpyrid-3-yl)methyl](2,2-difluorethyl)amino}furan-2(5H)-on known from WO 2007/115644), 4-{[(6-chlor-5-fluorpyrid-3-yl)methyl](methyl)amino}furan-2(5H)-on (known from WO 2007/115643), 4-{[(5,6-dichlorpyrid-3-yl)methyl](2-fluorethyl)amino}furan-2(5H)-on (known from WO 2007/115646), 4-{[(6-chlor-5-fluorpyrid-3-yl)methyl](cyclopropyl)amino}furan-2(5H)-on (known from WO 2007/115643), 4-{[(6-chlorpyrid-3-yl)methyl](cyclopropyl)amino}furan-2(5H)-on (known from EP-A-0 539 588), 4-{[(6-chlorpyrid-3-yl)methyl](methyl)amino}furan-2(5H)-on (known from EP-A-0 539 588)

Particularly preferred insect control agents are clothianidin, imidacloprid, thiacloprid, thiamethoxam, and acetamiprid.

A very particularly preferred insect control agent is imidacloprid.

Another very particularly preferred insect control agent is thiacloprid.

Another very particularly preferred insect control agent is thiamethoxam.

Another very particularly preferred insect control agent is acetamiprid.

The most particularly preferred insect control agent is clothianidin.

The ability of neonicotinoid compounds to increase plant growth, including root system development, independent of their pesticidal activity are further described in U.S. Pat. No. 6,753,296.

In an alternative embodiment, the inventive compositions optionally include an additional chemical compound with direct nematicidal activity to be utilized in combination with a biological control agent and at least one of the non-nematicidal insect control agents listed above. Suitable nematicidal insect control agents include antibiotic nematicides such as abamectin; carbamate nematicides such as benomyl, carbofuran, carbosulfan, and cloethocarb; oxime carbamate nematicides such as alanycarb, aldicarb, aldoxycarb, oxamyl; organophosphorus nematicides such as diamidafos, fenamiphos, fosthietan, phosphamidon, cadusafos, chlorpyrifos, dichlofenthion, dimethoate, ethoprophos, fensulfothion, fosthiazate, heterophos, isamidofos, isazofos, methomyl, phorate, phosphocarb, terbufos, thiodicarb, thionazin, triazophos, imicyafos, and mecarphon. Other suitable nematicidal insect control agents include acetoprole, benclothiaz, chloropicrin, dazomet, DBCP, DCIP, 1,2-dichloropropane, 1,3-dichloropropene, furfural, iodomethane, metam, methyl bromide, methyl isothiocyanate, and xylenols.

The amount of the at least one insect control agent employed in the compositions can vary depending on the final formulation as well as the size of the plant and seed to be treated. Preferably, the at least one insect control agent or fungicide is about 1% w/w to about 80% w/w based on the entire formulation. More preferably, the insect control agent or the fungicide is present in an amount of about 5% w/w to about 60% w/w and most preferably about 10% w/w to about 50% w/w.

Typically, the ratio of the biological control agent to an insect control agent or a fungicide is in the range of 100:1 and 1:100. Preferably, the ratio is in the range of 50:1 and 1:50. These ratio ranges are based on the assumption that the spore preparation of the biological control agent contains $10^{11}$/g. If spore preparations vary in density, the ratios have to be adapted accordingly to match the above listed ratio ranges. A ratio of 100:1 means 100 weight parts of the spore preparations of the biological control agent to 1 weight part of the insect control agent or fungicide.

Further, the compositions according to this invention contain one or more fungicides. These fungicides can be selected from the lists (F1) to (F14):

(F1) Inhibitors of the nucleic acid synthesis, for example benalaxyl, benalaxyl-M, bupirimate, clozylacon, dimethirimol, ethirimol, furalaxyl, hymexazol, metalaxyl, metalaxyl-M, ofurace, oxadixyl and oxolinic acid.

(F2) Inhibitors of the mitosis and cell division, for example benomyl, carbendazim, chlorfenazole, diethofencarb, ethaboxam, fuberidazole, pencycuron, thiabendazole, thiophanate, thiophanate-methyl and zoxamide.

(F3) Inhibitors of the respiration, for example diflumetorim as CI-respiration inhibitor; bixafen, boscalid, carboxin, fenfuram, flutolanil, fluopyram, furametpyr, furmecyclox, isopyrazam (9R-component), isopyrazam (9S-component), mepronil, oxycarboxin, penthiopyrad, thifluzamide as CII-respiration inhibitor; amisulbrom, azoxystrobin, cyazofamid, dimoxystrobin, enestroburin, famoxadone, fenamidone, fluoxastrobin, kresoxim-methyl, metominostrobin, orysastrobin, picoxystrobin, pyraclostrobin, pyribencarb, trifloxystrobin as CIII-respiration inhibitor.

(F4) Compounds capable to act as an uncoupler, like for example binapacryl, dinocap, fluazinam and meptyldinocap.

(F5) Inhibitors of the ATP production, for example fentin acetate, fentin chloride, fentin hydroxide, and silthiofam.

(F6) Inhibitors of the amino acid and/or protein biosynthesis, for example andoprim, blasticidin-S, cyprodinil, kasugamycin, kasugamycin hydrochloride hydrate, mepanipyrim and pyrimethanil (F7) Inhibitors of the signal transduction, for example fenpiclonil, fludioxonil and quinoxyfen.

(F8) Inhibitors of the lipid and membrane synthesis, for example biphenyl, chlozolinate, edifenphos, etridiazole, iodocarb, iprobenfos, iprodione, isoprothiolane, procymidone, propamocarb, propamocarb hydrochloride, pyrazophos, tolclofos-methyl and vinclozolin.

(F9) Inhibitors of the ergosterol biosynthesis, for example aldimorph, azaconazole, bitertanol, bromuconazole, cyproconazole, diclobutrazole, difenoconazole, diniconazole, diniconazole-M, dodemorph, dodemorph acetate, epoxiconazole, etaconazole, fenarimol, fenbuconazole, fenhexamid, fenpropidin, fenpropimorph, fluquinconazole, flurprimidol, flusilazole, flutriafol, furconazole, furconazole-cis, hexaconazole, imazalil, imazalil sulfate, imibenconazole, ipconazole, metconazole, myclobutanil, naftifine, nuarimol, oxpoconazole, paclobutrazol, pefurazoate, penconazole, piperalin, prochloraz, propiconazole, prothioconazole, pyributicarb, pyrifenox, quinconazole, simeconazole, spiroxamine, tebuconazole, terbinafine, tetraconazole, triadimefon, triadimenol, tridemorph, triflumizole, triforine, triticonazole, uniconazole, viniconazole and voriconazole.

(F10) Inhibitors of the cell wall synthesis, for example benthiavalicarb, dimethomorph, flumorph, iprovalicarb, mandipropamid, polyoxins, polyoxorim, prothiocarb, validamycin A, and valiphenal.

(F11) Inhibitors of the melanine biosynthesis, for example carpropamid, diclocymet, fenoxanil, phthalide, pyroquilon and tricyclazole.

(F12) Compounds capable to induce a host defence, like for example acibenzolar-S-methyl, probenazole, and tiadinil.

(F13) Compounds capable to have a multisite action, like for example bordeaux mixture, captafol, captan, chlorothalonil, copper naphthenate, copper oxide, copper oxychloride, copper preparations such as copper hydroxide, copper sulphate, dichlofluanid, dithianon, dodine, dodine free base, ferbam, fluorofolpet, folpet, guazatine, guazatine acetate, iminoctadine, iminoctadine albesilate, iminoctadine triacetate, mancopper, mancozeb, maneb, metiram, metiram zinc, oxine-copper, propamidine, propineb, sulphur and sulphur preparations including calcium polysulphide, thiram, tolylfluanid, zineb and ziram.

(F14) Further compounds like for example 2,3-dibutyl-6-chlorothieno[2,3-d]pyrimidin-4(3H)-one, ethyl (2Z)-3-amino-2-cyano-3-phenylprop-2-enoate, BYF 14182: (N-[2-(1,3-dimethyl-butyl)phenyl]-5-fluoro-1,3-dimethyl-1H-pyrazole-4-carboxamide), N-{2-[1,1'-bi(cyclopropyl)-2-yl]phenyl}-3-(difluoromethyl)-1-methyl-1H-pyrazole-4-carboxamide, 3-(difluoromethyl)-1-methyl-N-(3',4',5'-trifluorobiphenyl-2-yl)-1H-pyrazole-4-carboxamide, 3-(difluoromethyl)-N-[4-fluoro-2-(1,1,2,3,3,3-hexafluoropropoxy)phenyl]-1-methyl-1H-pyrazole-4-carboxamide, (2E)-2-(2-{[6-(3-chloro-2-methylphenoxy)-5-fluoropyrimidin-4-yl]oxy}phenyl)-2-(methoxyimino)-N-methylethanamide, (2E)-2-{2-[({[(2E,3E)-4-(2,6-dichlorophenyl)but-3-en-2-ylidene]amino}oxy)methyl]phenyl}-2-(methoxyimino)-N-methylethanamide, 2-chloro-N-(1,1,3-trimethyl-2,3-dihydro-1H-inden-4-yl)pyridine-3-carboxamide, N-(3-ethyl-3,5,5-trimethylcyclohexyl)-3-(formylamino)-2-hydroxybenzamide, 5-methoxy-2-methyl-4-(2-{[({(1E)-1-[3-(trifluoromethyl)phenyl]ethylidene}amino)oxy]methyl}phenyl)-2,4-dihydro-3H-1,2,4-triazol-3-one, (2E)-2-(methoxyimino)-N-methyl-2-(2-{[({(1E)-1-[3-(trifluoromethyl)phenyl]ethylidene}amino)oxy]methyl}phenyl)ethanamide, (2E)-2-(methoxyimino)-N-methyl-2-{2-[(E)-({1-[3-(trifluoromethyl)phenyl]ethoxy}imino) methyl]phenyl}ethanamide, (2E)-2-{2-[({[(1E)-1-(3-{[(E)-1-fluoro-2-phenylethenyl]oxy}phenyl)ethylidene]amino}oxy)methyl]phenyl}-2-(methoxyimino)-N-methylethanamide, 1-(4-chlorophenyl)-2-(1H-1,2,4-triazol-1-yl)cycloheptanol, methyl 1-(2,2-dimethyl-2,3-dihydro-1H-inden-1-yl)-1H-imidazole-5-carboxylate, N-ethyl-N-methyl-N'-{2-methyl-5-(trifluoromethyl)-4-[3-(trimethylsilyl)propoxy]phenyl}imidoformamide, N'-{5-(difluoromethyl)-2-methyl-4-[3-(trimethylsilyl)propoxy]phenyl}-N-ethyl-N-methylimidoformamide, O-{1-[(4-methoxyphenoxy)methyl]-2,2-dimethylpropyl}1H-imidazole-1-carbothioate, N-[2-(4-{[3-(4-chlorophenyl)prop-2-yn-1-yl]oxy}-3-methoxyphenyl)ethyl]-N$^2$-(methylsul-fonyl)valinamide, 5-chloro-7-(4-methylpiperidin-1-yl)-6-(2,4,6-trifluorophenyl)[1,2,4]triazolo[1,5-a]pyrimidine, 5-amino-1,3,4-thiadiazole-2-thiol, propamocarb-fosetyl, 1-[(4-methoxyphenoxy)methyl]-2,2-dimethylpropyl 1H-imidazole-1-carboxylate, 1-methyl-N-[2-(1,1,2,2-tetrafluoroethoxy)phenyl]-3-(trifluoromethyl)-1H-pyrazole-4-carboxamide, 2,3,5,6-tetrachloro-4-(methylsulfonyl)pyridine, 2-butoxy-6-iodo-3-propyl-4H-chromen-4-one, 2-phenylphenol and salts, 3-(difluoromethyl)-1-methyl-N-[2-(1,1,2,2-tetrafluoroethoxy)phenyl]-1H-pyrazole-4-carboxamide, 3,4,5-trichloropyridine-2,6-dicarbonitrile, 3-[5-(4-chlorophenyl)-2,3-dimethylisoxazolidin-3-yl] pyridine, 3-chloro-5-(4-chlorophenyl)-4-(2,6-difluorophenyl)-6-methylpyridazine, 4-(4-chlorophenyl)-5-(2,6-difluorophenyl)-3,6-dimethylpyridazine, quinolin-8-ol, quinolin-8-ol sulfate (2:1) (salt), 5-methyl-6-octyl-3,7-dihydro[1,2,4]triazolo[1,5-a]pyrimidin-7-amine, 5-ethyl-6-octyl-3,7-dihydro[1,2,4]triazolo[1,5-a]pyrimidin-7-amine, benthiazole, bethoxazin, capsimycin, carvone, chinomethionat, chloroneb, cufraneb, cyflufenamid, cymoxanil, cyprosulfamide, dazomet, debacarb, dichlorophen, diclomezine, dicloran, difenzoquat, difenzoquat methylsulphate, diphenylamine, ecomate, ferimzone, flumetover, fluopicolide, fluoroimide, flusulfamide, flutianil, fosetyl-aluminium, fosetyl-calcium, fosetyl-sodium, hexachlorobenzene, irumamycin, isotianil, methasulfocarb, methyl (2E)-2-{2-[({cyclopropyl[(4-methoxyphenyl)imino]methyl}thio)methyl]phenyl}-3-methoxyacrylate, methyl isothiocyanate, metrafenone, (5-bromo-2-methoxy-4-methylpyridin-3-yl)(2,3,4-trimethoxy-6-methylphenyl)-methanone, mildiomycin, tolnifanide, N-(4-chlorobenzyl)-3-[3-methoxy-4-(prop-2-yn-1-yloxy)phenyl]propanamide, N-[(4-chlorophenyl)(cyano)methyl]-3-[3-methoxy-4-(prop-2-yn-1-yloxy)phenyl]propanamide, N-[(5-bromo-3-chloropyridin-2-yl)methyl]-2,4-dichloropyridine-3-carboxamide, N-[1-(5-bromo-3-chloropyridin-2-yl)ethyl]-2,4-dichloropyridine-3-carboxamide, N-[1-(5-bromo-3-chloropyridin-2-yl)ethyl]-2-fluoro-4-iodopyridine-3-carboxamide, N-{(Z)-[(cyclopropylmethoxy)imino][6-(difluoromethoxy)-2,3-difluorophenyl]methyl}-2-phenylacetamide, N-{(E)-[(cyclopropylmethoxy)imino][6-(difluoromethoxy)-2,3-difluorophenyl]methyl}-2-phenylacetamide, natamycin, nickel dimethyldithiocarbamate, nitrothal-isopropyl, octhilinone, oxamocarb, oxyfenthiin, pentachlorophenol and salts, phenazine-1-carboxylic acid, phenothrin, phosphorous acid and its salts, propamocarb fosetylate, propanosine-sodium, proquinazid, pyrrolnitrine, quintozene, S-prop-2-en-1-yl 5-amino-2-(1-methylethyl)-4-(2-methylphenyl)-3-oxo-2,3-dihydro-1H-pyrazole-1-carbothioate, tecloftalam, tecnazene, triazoxide, trichlamide, 5-chloro-N'-phenyl-N'-prop-2-yn-1-ylthiophene-2-sulfonohydrazide and zarilamid.

Alternatively, compositions according to this invention comprise one biological control agent and at least one fungicide selected from groups (F1) to (F14).

Further, compositions according to this invention comprise one biological control agent, at least one insect control agent selected from groups (I1) to (I22) and at least one fungicide selected from groups (F1) to (F14).

In a preferred embodiment, the fungicides are selected from the following list:
Azoxystrobin, Boscalid, BYF 14182: (N-[2-(1,3-dimethylbutyl)phenyl]-5-fluoro-1,3-dimethyl-1H-pyrazole-4-carboxamide), Carbendazim, Carboxin, Fenamidone, Fludioxonil, Fluopicolide, Fluoxastrobin, Fluquinconazole, Flutriafol, Ipconazole, Iprodione, Isotianil, Mefenoxam, Metalaxyl, Pencycuron, Prochloraz, Prothioconazole, Pyraclostrobin, Pyrimethanil, Silthiopham, Tebuconazole, Thiram, Tolylfluanid, Triadimenol, Triazoxide, Trifloxystrobin, Triflumuron, Triticonazole, In a another preferred embodiment, the fungicide is N-{2-[1,1'-bi(cyclopropyl)-2-yl]phenyl}-3-(difluoromethyl)-1-methyl-1H-pyrazole-4-carboxamide.

Preferred compositions according to the invention comprise a biological control agent, which is *Bacillus firmus* strain CNCM I-1582 spore and at least one fungicide selected from the list (F1) to (F14).

In another preferred embodiment the compositions according to the invention comprise a biological control agent, which is *Bacillus cereus* strain CNCM I-1562 spore and at least one fungicide selected from the list (F1) to (F14).

Especially preferred compositions according to the invention comprise a biological control agent, which is *Bacillus firmus* strain CNCM I-1582 spore and at least one fungicide selected from the list: Azoxystrobin, Boscalid, BYF 14182, Carbendazim, Carboxin, Fenamidone, Fludioxonil, Fluopicolide, Fluoxastrobin, Fluquinconazole, Flutriafol, Ipconazole, Iprodione, Isotianil, Mefenoxam, Metalaxyl, Pencycuron, Prochloraz, Prothioconazole, Pyraclostrobin, Pyrimethanil, Silthiopham, Tebuconazole, Thiram, Tolylfluanid, Triadimenol, Triazoxide, Trifloxystrobin, Triflumuron, Triticonazole.

Most preferred fungicides according to the invention are: Fluoxastrobin, Ipconazole, Metalaxyl, Mefenoxam, Prothioconazole, Pyraclostrobin, Trifloxystrobin. BYF 14182, azoxystrobin.

Preferred combinations comprising a biological control agent and at least one insect control agent are the combinations (C1) or (C2) or any of (C1-9) to (C1-10):

(C1) Combinations wherein the biological control agent is *Bacillus firmus* CNCM I-1582 spore and the insect control agent is selected from the list: Clothianidin, imidacloprid, thiacloprid, thiamethoxam, acetamiprid, methiocarb, thiodicarb, beta-cyfluthrin, cyfluthrin, deltamethrin, tefluthrin, indoxacarb, spinosad, spinetoram, fipronil, ethiprole, emamectin-benzoate, avermectin, spirodiclofen, spiromesifen, spirotetramat, flubendiamide, (R),(S)-3-chloro-$N^1$-{2-methyl-4-[1,2,2,2-tetrafluoro-1-(trifluoromethyl)ethyl]phenyl}-$N^2$-(1-methyl-2-methylsulphonylethyl)phthalamide, chlorantraniliprole (Rynaxypyr), or Cyantraniliprole (Cyazypyr), sulfoxaflor, 4-{[(6-brompyrid-3-yl)methyl](2-fluorethyl)amino}furan-2(5H)-on (known from WO 2007/115644), 4-{[(6-fluorpyrid-3-yl)methyl](2,2-difluorethyl)amino}furan-2(5H)-on (known from WO 2007/115644), 4-{[(2-chlor-1,3-thiazol-5-yl)methyl](2-fluorethyl)amino}furan-2(5H)-on (known from WO 2007/115644), 4-{[(6-chlorpyrid-3-yl)methyl](2-fluorethyl)amino}furan-2(5H)-on (known from WO 2007/115644), 4-{[(6-chlorpyrid-3-yl)methyl](2,2-difluorethyl)amino}furan-2(5H)-on known from WO 2007/115644), 4-{[(6-chlor-5-fluorpyrid-3-yl)methyl](methyl)amino}furan-2(5H)-on (known from WO 2007/115643), 4-{[(5,6-dichlorpyrid-3-yl)methyl](2-fluorethyl)amino}furan-2(5H)-on (known from WO 2007/115646), 4-{[(6-chlor-5-fluorpyrid-3-yl)methyl](cyclopropyl)amino}furan-2(5H)-on (known from WO 2007/115643), 4-{[(6-chlorpyrid-3-yl)methyl](cyclopropyl)amino}furan-2(5H)-on (known from EP-A-0 539 588), 4-{[(6-chlorpyrid-3-yl)methyl](methyl)amino}furan-2(5H)-on (known from EP-A-0 539 588), [(6-chlorpyridin-3-yl)methyl](methyl)oxido-$\lambda^4$-sulfanylidencyanamid (known from WO 2007/149134), [1-(6-chlorpyridin-3-yl)ethyl](methyl)oxido-$\lambda^4$-sulfanylidencyanamid (known from WO 2007/149134) and its diastereomeres (A) and (B).

(C2) Combinations wherein the biological control agent is *Bacillus firmus* CNCM I-1582 spore and the insect control agent is selected from the list: Clothianidin, imidacloprid, thiacloprid, thiamethoxam, acetamiprid, methiocarb, thiodicarb, beta-cyfluthrin, cyfluthrin, deltamethrin, tefluthrin, indoxacarb, spinosad, spinetoram, fipronil, ethiprole, emamectin-benzoate, avermectin, spirodiclofen, spiromesifen, spirotetramat, flubendiamide, (R),(S)-3-chloro-$N^1$-{2-methyl-4-[1,2,2,2-tetrafluoro-1-(trifluoromethyl)ethyl]phenyl}-$N^2$-(1-methyl-2-methylsulphonylethyl)phthalamide, chlorantraniliprole (Rynaxypyr), or Cyantraniliprole (Cyazypyr), sulfoxaflor, 4-{[(6-brompyrid-3-yl)methyl](2-fluorethyl)amino}furan-2(5H)-on (known from WO 2007/115644), 4-{[(6-fluorpyrid-3-yl)methyl](2,2-difluorethyl)amino}furan-2(5H)-on (known from WO 2007/115644), 4-{[(2-chlor-1,3-thiazol-5-yl)methyl](2-fluorethyl)amino}furan-2(5H)-on (known from WO 2007/115644), 4-{[(6-chlorpyrid-3-yl)methyl](2-fluorethyl)amino}furan-2(5H)-on (known from WO 2007/115644), 4-{[(6-chlorpyrid-3-yl)methyl](2,2-difluorethyl)amino}furan-2(5H)-on known from WO 2007/115644), 4-{[(6-chlor-5-fluorpyrid-3-yl)methyl](methyl)amino}furan-2(5H)-on (known from WO 2007/115643), 4-{[(5,6-dichlorpyrid-3-yl)methyl](2-fluorethyl)amino}furan-2(5H)-on (known from WO 2007/115646), 4-{[(6-chlor-5-fluorpyrid-3-yl)methyl](cyclopropyl)amino}furan-2(5H)-on (known from WO 2007/115643), 4-{[(6-chlorpyrid-3-yl)methyl](cyclopropyl)amino}furan-2(5H)-on (known from EP-A 0 539 588), 4-{[(6-chlorpyrid-3-yl)methyl](methyl)amino}furan-2(5H)-on (known from EP-A 0 539 588), [(6-chlorpyridin-3-yl)methyl](methyl)oxido-$\lambda^4$-sulfanylidencyanamid (known from WO 2007/149134), [1-(6-chlorpyridin-3-yl)ethyl](methyl)oxido-$\lambda^4$-sulfanylidencyanamid (known from WO 2007/149134) and its diastereomeres (A) and (B)

(C1-1) Combinations wherein the biological control agent is *Bacillus firmus* CNCM I-1582 spore and the insect control agent is comprised of clothianidin.

(C1-2) Combinations wherein the biological control agent is *Bacillus firmus* CNCM I-1582 spore and the insect control agent is comprised of imidacloprid.

(C1-3) Combinations wherein the biological control agent is *Bacillus firmus* CNCM I-1582 spore and the insect control agent is comprised of clothianidin and imidacloprid.

(C1-4) Combinations wherein the biological control agent is *Bacillus firmus* CNCM I-1582 spore and the insect control agent is comprised of clothianidin and (3-cyfluthrin.

(C1-5) Combinations wherein the biological control agent is *Bacillus firmus* CNCM I-1582 spore and the insect control agent is comprised of thiamethoxam and tefluthrin.

(C1-6) Combinations wherein the biological control agent is *Bacillus firmus* CNCM I-1582 spore and the insect control agent is comprised of clothianidin and imidacloprid.

(C1-7) Combinations wherein the biological control agent is *Bacillus firmus* CNCM I-1582 spore and the insect control agent is comprised of either thiodicarb and imidacloprid or thiodicarb and clothianidin.

(C1-8) Combinations wherein the biological control agent is *Bacillus firmus* CNCM I-1582 spore and the insect control agent is comprised of either Clothianidin and fipronil or fipronil and imidacloprid.

(C1-9) Combinations wherein the biological control agent is *Bacillus firmus* CNCM I-1582 spore and the insect control agent is comprised of
a) chlorantraniliprole and
b) imidacloprid or clothianidin or thiamethoxam or thiacloprid or acetamiprid or nitenpyram or sulfoxaflor or one of the compounds selected from the list 4-{[(6-brompyrid-3-yl)methyl](2-fluorethyl)amino}furan-2(5H)-on (known from WO 2007/115644), 4-{[(6-fluorpyrid-3-yl)methyl](2,2-difluorethyl)amino}furan-2(5H)-on (known from WO 2007/115644), 4-{[(2-chlor-1,3-thiazol-5-yl)methyl](2-fluorethyl)amino}furan-2(5H)-on (known from WO 2007/115644), 4-{[(6-chlorpyrid-3-yl)methyl](2-fluorethyl)amino}furan-2(5H)-on (known from WO 2007/115644), 4-{[(6-chlorpyrid-3-yl)methyl](2,2-difluorethyl)amino}furan-2(5H)-on known from WO 2007/115644), 4-{[(6-chlor-5-fluorpyrid-3-yl)methyl](methyl)amino}furan-2(5H)-on (known from WO 2007/115643), 4-{[(5,6-dichlorpyrid-3-yl)methyl](2-fluorethyl)amino}furan-2(5H)-on (known from WO 2007/115646), 4-{[(6-chlor-5-fluorpyrid-3-yl)methyl](cyclopropyl)amino}furan-2(5H)-on (known from WO 2007/115643), 4-{[(6-chlorpyrid-3-yl)methyl](cyclopropyl)amino}furan-2(5H)-on (known from EP-A-0 539 588), 4-{[(6-chlorpyrid-3-yl)methyl](methyl)amino}furan-2(5H)-on (known from EP-A-0 539 588), [(6-chlorpyridin-3-yl)methyl](methyl)oxido-$\lambda^4$-sulfanylidencyanamid (known from WO 2007/149134), [1-(6-chlorpyridin-3-yl)ethyl](methyl)oxido-$\lambda^4$-sulfanylidencyanamid (known from WO 2007/149134) and its diastereomeres (A) and (B).

(C1-10) Combinations wherein the biological control agent is *Bacillus firmus* CNCM I-1582 spore and the insect control agent is comprised of
a) Cyantraniliprole
b) imidacloprid or clothianidin or thiamethoxam or thiacloprid or acetamiprid or nitenpyram or sulfoxaflor or one of the compounds selected from the list 4-{[(6-brompyrid-3-yl)methyl](2-fluorethyl)amino}furan-2(5H)-on (known from WO 2007/115644), 4-{[(6-fluorpyrid-3-yl)methyl](2,2-difluorethyl)amino}furan-2(5H)-on (known from WO 2007/115644), 4-{[(2-chlor-1,3-thiazol-5-yl)methyl](2-fluorethyl)amino}furan-2(5H)-on (known from WO 2007/115644), 4-{[(6-chlorpyrid-3-yl)methyl](2-fluorethyl)amino}furan-2(5H)-on (known from WO 2007/115644), 4-{[(6-chlorpyrid-3-yl)methyl](2,2-difluorethyl)amino}furan-2(5H)-on known from WO 2007/115644), 4-{[(6-chlor-5-fluorpyrid-3-yl)methyl](methyl)amino}furan-2(5H)-on (known from WO 2007/115643), 4-{[(5,6-dichlorpyrid-3-yl)methyl](2-fluorethyl)amino}furan-2(5H)-on (known from WO 2007/115646), 4-{[(6-chlor-5-fluorpyrid-3-yl)methyl](cyclopropyl)amino}furan-2(5H)-on (known from WO 2007/115643), 4-{[(6-chlorpyrid-3-yl)methyl](cyclopropyl)amino}furan-2(5H)-on (known from EP-A-0 539 588), 4-{[(6-chlorpyrid-3-yl)methyl](methyl)amino}furan-2(5H)-on (known from EP-A-0 539 588), [(6-chlorpyridin-3-yl)methyl](methyl)oxido-$\lambda^4$-sulfanylidencyanamid (known from WO 2007/149134), [1-(6-chlorpyridin-3-yl)ethyl](methyl)oxido-$\lambda^4$-sulfanylidencyanamid (known from WO 2007/149134) and its diastereomeres (A) and (B).

Further embodiments according to the invention comprise compositions, wherein the biological control agent in any of the compositions (C1), (C2), (C1-1) to (C1-10), instead of *Bacillus firmus* CNCM I-1582 spore, is any member of Group B.

In a further embodiment, the compositions disclosed in this invention can contain an isoflavone. Isoflavones are plant chemicals which occur largely in members of the Leguminosae plant family. They are based on a simple diphenolic ring structure as described for example by Carlson et al (1980) Journal of Chromatography, 198, 193-197 and U.S. Pat. No. 7,033,621, the contents of which are incorporated by reference. Examples of isoflavones useful in component (It) of the present invention include, but are not limited to, genistein, biochanin A, 10 formononetin, daidzein. glycitein, hesperetin, naringenin, chalcone, coumarin, Ambiol(2-methyl-4-[dimethylaminomethyl]-5-hydro-, ascorbate and pratensein and the salts and esters thereof. Formononetin, hesperetin, naringenin, and salts, esters and mixtures thereof are preferred isoflavones.

In a preferred embodiment, an isoflavone is mixed with the compositions (C1), C(2), (C1-1) to (C1-10).

An especially preferred isoflavone is formononetin either as a salt or the free acid.

In a further embodiment, the compositions disclosed in this invention can contain an inoculant, in particular a soil inoculant. Examples for such inoculants are Bacteria of the genus *Rhizobium, Pseudomonas, Azospirillum, Azotobacter, Streptomyces, Burkholdia, Agrobacterium*, Endo-, Ecto-, Vesicular-Arbuscular (VA) Mycorhizza In a preferred embodiment, an inoculant is mixed with one of the compositions (C1), C(2), (C1-1) to (C1-10).

The present invention also provides methods of treating a plant by application of any of a variety of customary formulations in an effective amount to either the soil (i.e., in-furrow), a portion of the plant (i.e., drench) or on the seed before planting (i.e., seed coating or dressing). Customary formulations include solutions (SL), emulsifiable concentrate (EC), wettable powders (WP), suspension concentrate (SC and FS), wettable powder (WP), soluble powders (SP), granules (GR), suspension-emulsion concentrate (SE), natural and synthetic materials impregnated with active compound, and very fine control release (CR) capsules in polymeric substances. In one embodiment, the insect control agent and biological control agent are formulated in powders that are available in either a ready-to-use formulation or are mixed together at the time of use. In either embodiment, the powder may be admixed with the soil prior to or at the time of planting. In an alternative embodiment, one or both of either the biological control agent or insect control agent is a liquid formulation that is mixed together at the time of treating. One of ordinary skill in the art understands that an effective amount of the inventive compositions depends on the final formulation of the composition as well as the size of the plant or the size of the seed to be treated. Depending on the final formulation and method of application, one or more suitable additives can also be introduced to the present compositions. Adhesives such as carboxymethylcellulose and natural and synthetic polymers in the form of powders, granules or latexes, such as gum arabic, chitin, polyvinyl alcohol and polyvinyl acetate, as well as natural phospholipids, such as cephalins and lecithins, and synthetic phospholipids, can be added to the present compositions.

In a preferred embodiment, the compositions are formulated in a single, stable solution, or emulsion, or suspension. For solutions, the active chemical compounds (i.e., the insect control agent) are dissolved in solvents before the biological control agent is added. Suitable liquid solvents include petroleum based aromatics, such as xylene, toluene or alkylnaphthalenes, aliphatic hydrocarbons, such as cyclohexane or paraffins, for example petroleum fractions, mineral and vegetable oils, alcohols, such as butanol or glycol as well as their ethers and esters, ketones, such as methyl ethyl ketone, methyl isobutyl ketone or cyclohexanone, strongly polar solvents, such as dimethylformamide and dimethyl sulphoxide. For emulsion or suspension, the liquid medium is water. In one embodiment, the insect control agent and biological control agent are suspended in separate liquids and mixed at the time of application. In a preferred embodiment of suspension, the insect control agent and biologic are combined in a ready-to-use formulation that exhibits a shelf-life of at least two years. In use, the liquid can be sprayed or atomized foliarly or in-furrow at the time of planting the crop. The liquid composition can be introduced to the soil before germination of the seed or directly to the soil in contact with the roots by utilizing a variety of techniques including, but not limited to, drip irrigation, sprinklers, soil injection or soil drenching.

Optionally, stabilizers and buffers can be added, including alkaline and alkaline earth metal salts and organic acids, such as citric acid and ascorbic acid, inorganic acids, such as hydrochloric acid or sulfuric acid. Biocides can also be added and can include formaldehydes or formaldehyde-releasing agents and derivatives of benzoic acid, such as p-hydroxybenzoic acid.

In one embodiment, the solid or liquid compositions further contain functional agents capable of protecting seeds from the harmful effects of selective herbicides such as activated carbon, nutrients (fertilizers), and other agents capable of improving the germination and quality of the products or a combination thereof.

In a particularly preferred embodiment, the compositions of the present invention are formulated as a seed treatment. The seed treatment comprises at least one insect control agent and at least one biological control agent. According to the present invention, the seeds are substantially uniformly coated with one or more layers of the compositions disclosed herein using conventional methods of mixing, spraying or a combination thereof through the use of treatment application equipment that is specifically designed and manufactured to accurately, safely, and efficiently apply seed treatment products to seeds. Such equipment uses various types of coating technology such as rotary coaters, drum coaters, fluidized bed techniques, spouted beds, rotary mists or a combination thereof. Liquid seed treatments such as those of the present invention can be applied via either a spinning "atomizer" disk or a spray nozzle which evenly distributes the seed treatment onto the seed as it moves though the spray pattern. Preferably, the seed is then mixed or tumbled for an additional period of time to achieve additional treatment distribution and drying. The seeds can be primed or unprimed before coating with the inventive compositions to increase the uniformity of germination and emergence. In an alternative embodiment, a dry powder formulation can be metered onto the moving seed and allowed to mix until completely distributed.

The seeds may be coated via a batch or continuous coating process. In a continuous coating embodiment, continuous flow equipment simultaneously meters both the seed flow and the seed treatment products. A slide gate, cone and orifice, seed wheel, or weighing device (belt or diverter) regulates seed flow. Once the seed flow rate through treating equipment is determined, the flow rate of the seed treatment is calibrated to the seed flow rate in order to deliver the desired dose to the seed as it flows through the seed treating equipment. Additionally, a computer system may monitor the seed input to the coating machine, thereby maintaining a constant flow of the appropriate amount of seed.

In a batch coating embodiment, batch treating equipment weighs out a prescribed amount of seed and places the seed into a closed treating chamber or bowl where the corresponding dose of seed treatment is then applied. This batch is then dumped out of the treating chamber in preparation for the treatment of the next batch. With computer control systems, this batch process is automated enabling it to continuously repeat the batch treating process.

In either embodiment, the seed coating machinery can optionally be operated by a programmable logic controller that allows various equipment to be started and stopped without employee intervention. The components of this system are commercially available through several sources such as Gustafson Equipment of Shakopee, Minn.

A variety of additives can be added to the seed treatment formulations comprising the inventive compositions. Binders can be added and include those composed preferably of an adhesive polymer that can be natural or synthetic without phytotoxic effect on the seed to be coated. Any of a variety of colorants may be employed, including organic chromophores classified as nitroso, nitro, azo, including monoazo, bisazo and polyazo, diphenylmethane, triarylmethane, xanthene, methine, acridine, thiazole, thiazine, indamine, indophenol, azine, oxazine, anthraquinone and phthalocyanine. Other additives that can be added include trace nutrients such as salts of iron, manganese, boron, copper, cobalt, molybdenum and zinc. A polymer or other dust control agent can be applied to retain the treatment on the seed surface.

Other conventional seed treatment additives include, but are not limited to, coating agents, wetting agents, buffering agents, and polysaccharides. At least one agriculturally acceptable carrier can be added to the seed treatment formulation such as water, solids or dry powders. The dry powders can be derived from a variety of materials such as calcium carbonate, gypsum, vermiculite, talc, humus, activated charcoal, and various phosphorous compounds.

In one embodiment, the seed coating composition can comprise at least one filler which is an organic or inorganic, natural or synthetic component with which the active components are combined to facilitate its application onto the seed. Preferably, the filler is an inert solid such as clays, natural or synthetic silicates, silica, resins, waxes, solid fertilizers (for example ammonium salts), natural soil minerals, such as kaolins, clays, talc, lime, quartz, attapulgite, montmorillonite, bentonite or diatomaceous earths, or synthetic minerals, such as silica, alumina or silicates, in particular aluminium or magnesium silicates.

Any plant seed capable of germinating to form a plant that is susceptible to attack by nematodes and/or pathogenic fungi can be treated in accordance with the invention. Suitable seeds include those of cole crops, vegetables, fruits, trees, fiber crops, oil crops, tuber crops, coffee, flowers, legume, cereals, as well as other plants of the monocotyledonus, and dicotyledonous species. Preferably, crop seeds are be coated which include, but are not limited to, soybean, peanut, tobacco, grasses, wheat, barley, rye, sorghum, rice, rapeseed, sugarbeet, sunflower, tomato, pepper, bean, lettuce, potato, and carrot seeds. Most preferably, cotton or corn (sweet, field, seed, or popcorn) seeds are coated with the present compositions.

The compositions in accordance with the present invention exhibit unexpectedly improved overall plant vigor and yield by combining agriculturally effective amounts of at least one environmentally friendly biological control agent and at least one insect control agent. These unexpected results are attributed to the combination of the nematicidal and/or fungicidal properties of the biological control agent and the root-mass enhancing properties of the insect control agent.

A further advantage is the synergistic increase in insecticidal and/or fungicidal activity of the agents of the invention in comparison to the respective individual active compounds, which extends beyond the sum of the activity of both individually applied active compounds. In this way an optimization of the amount of active compound applied is made possible.

It is also be regarded as advantageous that the combinations of the invention can also be used in particular with transgenic seeds whereby the plants emerging from this seed are capable of the expression of a protein directed against pests and pathogens. By treatment of such seed with the agents of the invention certain pests and pathogens can already be controlled by expression of the, for example, insecticidal protein, and it is additionally surprising that a synergistic activity supplementation occurs with the agents of the invention, which improves still further the effectiveness of the protection from pest and pathogen infestation.

The agents of the invention are suitable for the protection of seed of plant varieties of all types as already described which are used in agriculture, in greenhouses, in forestry, in garden construction or in vineyards. In particular, this concerns seed of maize, peanut, canola, rape, poppy, olive, coconut, cacao, soy cotton, beet, (e.g. sugar beet and feed beet), rice, millet, wheat, barley, oats, rye, sunflower, sugar cane or tobacco. The agents of the invention are also suitable for the treatment of the seed of fruit plants and vegetables as previously described. Particular importance is attached to the treatment of the seed of maize, soy, cotton, wheat and canola or rape. Thus, for example, the combination of number (1) is particularly suitable for the treatment of maize seed.

As already described, the treatment of transgenic seed with an agent of the invention is of particular importance. This concerns the seeds of plants which generally contain at least one heterologous gene that controls the expression of a polypeptide with special insecticidal properties. The heterologous gene in transgenic seed can originate from microorganisms such as *Bacillus*, *Rhizobium*, *Pseudomonas*, *Serratia*, *Trichoderma*, *Clavibacter*, *Glomus* or *Gliocladium*. The present invention is particularly suitable for the treatment of transgenic seed that contains at least one heterologous gene that originates from *Bacillus* sp. and whose gene product exhibits activity against the European corn borer and/or western corn rootworm. Particularly preferred is a heterologous gene that originates from *Bacillus thuringiensis*.

The bacterial spores surprisingly not only retain their nematicidal and/or fungicidal properties in the presence of a chemical insect control agent but demonstrate an enhanced ability to colonize the plant's root system. This enhanced ability leads to the amplification of their nematicidal and/or fungicidal activity and thus the result is improved vigor which, in turn, results in improved yield.

Advantages of the present invention will be apparent from the description of the non-limiting examples that follow. The following examples exhibit merely a preferred embodiment of the present invention. As the following examples demonstrate, the compositions in accordance with the present invention exhibit unexpectedly improved overall plant vigor and yield by combining agriculturally effective amounts of at least one environmentally friendly biological control agent and at least one insect control agent. These unexpected results are attributed to the combination of the nematicidal and/or fungicidal properties of the biological control agent and the root-mass enhancing properties of the insect control agent. As further demonstrated in the following examples, the bacterial spores surprisingly not only retain their nematicidal and/or fungicidal properties in the presence of a chemical insect control agent but demonstrate an enhanced ability to colonize the plant's root system. This enhanced ability leads to the amplification of their nematicidal and/or fungicidal activity and thus the result is improved vigor which, in turn, results in improved yield.

EXAMPLE 1

Experiments were designed to illustrate the ability of certain bacteria to colonize root systems. In this particular experiment, both untreated cotton seeds and cotton seeds treated with spores of *Bacillus firmus* (a biological nematicide) were planted in autoclaved soil to minimize natural flora. The seedlings were harvested three weeks later. Using sterile water and a stomacher, root systems were processed to recover the bacteria.

While all of the samples contained multiple species of bacteria, B. firmus was only isolated from the root systems of plants grown from the treated seed. This experiment illustrated that the B. firmus, when utilized as a seed treatment, was able to grow and proliferate within the rhizosphere.

EXAMPLE 2

The experiment of Example 1 was then conducted with an altered recovery method. At harvest, half of the root systems from the treated seed were rinsed in sterile water for 30 seconds and instead of using a stomacher, the entire root system was placed directly onto a tryptic soy agar plate. B. firmus was again not recovered from the untreated samples and while it was recovered from the un-rinsed root systems of plants grown from the treated seed, it was not consistently the predominant bacterial species recovered. In the rinsed root systems however, B. firmus was not only recovered but proved to be consistently the predominant bacteria species. This experiment illustrated that B. firmus, when utilized as a seed treatment, is not only able to grow and proliferate within the rhizosphere but is actually capable of colonizing root systems. Similar experiments were also conducted with other agriculturally beneficial bacteria to prove root colonization.

To further substantiate that the bacteria recovered from the rinsed root systems of this experiment was the same species and strain used in the original treatment, a 500 base pair DNA analysis and RNA comparisons were performed. The results of this testing indicated that the recovered bacteria was not only the same species but had an indistinguishable RiboPrint pattern from the bacteria used in the treatment of the seed.

EXAMPLE 3

An experiment was performed to demonstrate that root system enhancements were obtained through the use of neonicotinoid insecticides. In this experiment cotton seed was treated with a fungicide base and one of three commonly used neonicotinoid insecticides: imidacloprid (sold under the trademark GAUCHO 600@0.375 mg ai/seed), clothianidin (sold under the trademark PONCHO 600@0.375 mg ai/seed), and thiomethoxam (sold under the trademark CRUISER@0.34 mg ai/seed).

TABLE 1

|  | Length (cm) | SurfArea (cm$^2$) | Volume (cm$^3$) | T/F/C |
|---|---|---|---|---|
| CTRL | 66.11 b | 11.66 b | 0.17 b | 47.53 b |
| Imidacloprid | 92.56 a | 20.11 a | 0.35 a | 85.60 a |
| Clothianidin | 88.11 a | 16.77 a | 0.29 a | 93.93 a |
| Thiomethoxam | 95.01 a | 17.43 a | 0.28 a | 77.17 a |

CTRL stands for control

Fifty seeds from each of the four treatments were planted. Plants were grown in standard soil in an indoor, temperature controlled, growth chamber and did not experience any significant disease or insect pressure. Seedlings were harvested 28 days after planting and analyzed using the WinRhizo® root analysis system. There was no significant difference in germination.

In Table 1, a comparison of Length, Surface Area, Volume, and Tips/Forks/Crossings, was made through the analysis of 40-45 plants per treatment and by averaging 10 repetitions bracketing the median for each category. Although there was variation both within the categories and within the treatments, the results showed all of the neonicotinoid insecticides provided a statistically significant growth response over the base treatment in each of the four categories based on LSD (least significant difference) and a 5% margin of error.

EXAMPLE 4

The following experiment was performed to demonstrate the unexpected nematicidal benefits achieved by combining biological nematicides with non-nematicidal neonicotinoid insecticides. Soybeans (Variety-S2743-4RR) were planted with a base fungicide package and imidacloprid (sold under the trademark GAUCHO 600@62.5 gm AI/100 kg), a biological nematicide, or a combination of both. The seed were then planted in standard soil and soil infested with Soybean Cyst nematodes. Plants were harvested 28 days later (~50 plants/treatment/soil type) and compared by height and by a WinRhizo® root system analysis (length, surface area, volume, tips, forks, and crossings (T/F/C))

TABLE 2

|  | Length (cm) | SurfArea (cm$^2$) | Volume (cm$^3$) | T/F/C | Height (cm) | % difference |
|---|---|---|---|---|---|---|
| 1.) NI | 281.93 | 66.40 | 1.25 | 497.68 | 26.78 |  |
| 2.) NI(SCN) | 167.41 | 44.51 | 0.97 | 283.90 | 19.09 | 52.52% |
| 3.) BN | 339.82 | 80.01 | 1.52 | 681.73 | 27.90 |  |
| 4.) BN(SCN) | 258.61 | 69.86 | 1.53 | 475.35 | 22.33 | 22.69% |
| 5.) NI/BN | 315.53 | 74.92 | 1.43 | 587.70 | 26.01 |  |
| 6.) NI/BN(SCN) | 337.09 | 69.21 | 1.17 | 550.55 | 24.14 | 7.81% |

1.) NI - Neonicotinoid Insecticide,
2.) NI(SCN) - Neonicotinoid Insecticide w/Soybean Cyst Nematodes,
3.) BN - Biological Nematicide,
4.) BN(SCN) - Biological Nematicide w/Soybean Cyst Nematodes,
5.) NI/BN - Neonicotinoid Insecticide and Biological Nematicide,
6.) NI/BN(SCN) - Neonicotinoid Insecticide and Biological Nematicide w/Soybean Cyst Nematodes The final column of Table 2 compares the total average percent difference in each of the treatments with soybean cyst nematode pressure. The plants with the insecticide alone fared the worst with stunted growth both above and below the soil and a total average reduction of 53%. The biological nematicide did exhibit nematode control having less than half the percent difference at 23%. The best overall treatment contained both the biological nematicide and the insecticide and there was only an 8% difference in overall plant development.

The insecticide alone while having no direct nematicidal activity, does seem to impact and enhance the nematicidal activity of the biological nematicide.

EXAMPLE 5

There are many factors to consider when analyzing yield data and comparative studies can be difficult due to the fact that environmental conditions and presence or lack of diverse disease/nematode/insect pressure(s) can fluctuate even within the same field. Although variability exists, by looking at a large enough data set, patterns begin to emerge.

Table 3 illustrates averages from 10 field trials where yield was compared between a chemical fungicide control (base) and the base treatment with, a biological fungicide, a neonicotinoid insecticide, and a combination of both the biological fungicide and the neonicotinoid insecticide. Table 3 also includes 7 field trials from a similar protocol except these trials where planted in areas of known nematode infestation and a biological nematicide was used instead of the biological fungicide. These 17 trials include averages from all of the data collected from these two protocols in 2007.

TABLE 3

| Average of 10 biological fungicide field trials in 2007 | | Average of 7 biological nematicide field trials in 2007 | |
|---|---|---|---|
| | Yield/BU | % improvement | | Yield/BU | % improvement |
| FC | 60.84 | | FC | 41.48 | |
| FC/BF | 60.82 | −0.03% | FC/BN | 42.81 | 3.10% |
| FC/NI | 62.07 | 2.02% | FC/NI | 42.27 | 1.91% |
| FC/NI/BF | 63.23 | 3.93% | FC/NI/BN | 43.67 | 5.27% |

FC = Fungicide Control, BF = Biological Fungicide, BN = Biological Nematicide, NI = Neonicotinoid Insecticide Using an equation taken from Colby's formula for synergy (found in the article "Calculating Synergistic and Antagonistic Responses of Herbicide Combinations", by S. R. Colby, Apr. 11, 1966, Scientific Article No. A 1271 Maryland Agricultural Experiment Station, Department of Agronomy, University of Maryland, College Park, Md.), the expected percent increase in yield from the combination of the biological control agents and neonicotinoid insecticides (E) is calculated using the percent increase in yield obtained from the use of the biological control agents alone (P1) and the percent increase in yield obtained from the use of the neonicotinoid insecticide alone (P2).

$$E=P1+P2-(P1(P2)/100)$$

Applying the equation to the trials above, the expected percent increase for the combination treatment in the fungicide trials would have been 1.99% (however the actual increase was 3.93%) and the expected percent increase in the combination treatment for the nematicide trials would be 4.95% (however the actual increase was 5.27%).

Having disclosed the subject matter of the present invention, it should be apparent that many modifications, substitutions and variations of the present invention are possible in light thereof. It is to be understood that the present invention can be practiced other than as specifically described. Such modifications, substitutions and variations are intended to be within the scope of the present application. As used in the following claims, articles such as "a", "the" and so on can connote the singular or the plural of the object following.

The invention claimed is:

1. A composition comprising a biological control agent and at least one insect control agent, wherein the biological control agent is *Bacillus firmus* CNCM I-1582 spores, wherein the at least one insect control agent is selected from the group consisting of clothianidin, imidacloprid, and thiamethoxam, and wherein the weight ratio of the biological control agent to the at least one insect control agent is between 50:1 and 1:50, wherein the at least one insect control agent is present in an amount from about 1% w/w to about 80% w/w based on the entire composition, and wherein the ratio is based on a preparation of spores containing $10^{11}$ spores/g of spore preparation.

2. A composition according to claim 1 further comprising a fungicide.

3. The composition according to claim 1 further comprising an isoflavone or a soil inoculant.

4. A seed treatment formulation comprising the composition according to claim 1.

5. A spray formulation for drench or in-furrow application comprising the composition according to claim 1.

6. The composition according to claim 1, comprising the *Bacillus firmus* CNCM I-1582 spores and clothianidin.

7. The composition according to claim 1, comprising the *Bacillus firmus* CNCM I-1582 spores and thiamethoxam.

8. The composition according to claim 1, comprising the *Bacillus firmus* CNCM I-1582 spores and imidacloprid.

* * * * *